United States Patent [19]
Garrison

[11] Patent Number: 5,188,148
[45] Date of Patent: Feb. 23, 1993

[54] CONDUIT PLATE FOR FLUID DELIVERY SYSTEM

[75] Inventor: Brevard S. Garrison, Reading, Mass.

[73] Assignee: Millipore Corporation, Bedford, Mass.

[21] Appl. No.: 655,012

[22] Filed: Feb. 14, 1991

Related U.S. Application Data

[63] Continuation-in-part of Ser. No. 633,713, Dec. 21, 1990.

[51] Int. Cl.$^5$ .............................................. F16K 27/00
[52] U.S. Cl. .................................. 137/606; 137/315; 251/331; 251/367
[58] Field of Search ............... 137/606, 315, 597, 607; 251/331, 367; 403/359; 285/360, 361, 376, 396

[56]   References Cited
   U.S. PATENT DOCUMENTS

| | | | |
|---|---|---|---|
| 4,008,736 | 2/1977 | Wittmann-Liebold et al. | 137/606 |
| 4,168,724 | 9/1979 | Graffunder et al. | 137/238 X |
| 4,298,020 | 11/1981 | Inada et al. | 251/367 X |
| 4,558,845 | 12/1985 | Hunkapiller | 137/606 X |
| 4,658,858 | 4/1987 | Beale | 137/606 |
| 4,773,446 | 9/1988 | Farnsworth et al. | 137/208 X |
| 4,874,014 | 10/1989 | Grant et al. | 137/606 |

Primary Examiner—Alan Cohan
Assistant Examiner—Kevin L. Lee
Attorney, Agent, or Firm—Andrew T. Karnakis; Paul J. Cook

[57]    ABSTRACT

A plate structure including conduit and reagent delivery means for a fluid delivery system is provided to deliver precise volumes of a plurality of fluids in sequence to a treatment reservoir. Fluid channels are formed in the plate structure to provide a means for delivering fluids from a plurality of fluid reservoirs attached to the plate structure to one or a plurality of treatment reservoirs attached to the plate structure. Each fluid is delivered by a system comprising a check valve in fluid communication with a fluid reservoirs, a positive displacement pump in fluid communication with the check valve and an injector in fluid communication with the positive displacement pump all of which are attached to the plate structure. A partition switch attached to the plate structure is provided to direct fluid to the desired treatment reservoirs or pressure reservoirs.

16 Claims, 6 Drawing Sheets

CONDUIT PLATE FOR FLUID DELIVERY SYSTEM

REFERENCE TO RELATED APPLICATION

This application is a continuation-in-part of application Ser. No. 633,713, filed Dec. 21, 1990.

BACKGROUND OF THE INVENTION

This invention relates to a plate structure for use in fluid delivery system for delivering a plurality of fluids, in sequence to a treatment reservoir.

Prior to the present invention, fluid delivery systems have been available which minimize intermixing of fluids while delivering a precise amount of a fluid for chemical reaction. These systems are generally utilized for chemical processes involving a large number of sequentially effected chemical reactions such as in protein synthesis, DNA synthesis or when sequencing proteins.

U.S. Pat. No. 4,008,736 discloses a valve block containing a capillary formed of capillary segments bored at about 30° from a contact surface of the block. The junctions of the capillary segments are effected at the contact surface and within the block. The junctions at the contact surfaces form valving sites to which are engaged apertured sliding blocks which effect fluid communication with the capillary. While the sliding blocks are effective in providing the desired fluid flow, they wear rapidly thereby causing undesirable leaks.

U.S. Pat. No. 4,168,724 discloses a similar device but replaces the slider valves with diaphragm valves. The fluid is delivered through the valves from a pressurized fluid storage source. This system requires a vacuum assist to open the valves. This system is undesirable because the type of diaphragm valve used is undesirably susceptible to particulate contamination. In addition, the pressure drop through the valves is difficult to control which causes inaccurate reagent delivery.

U.S. Pat. No. 4,558,845 discloses a fluid delivery system utilizing a valve block assembly comprising a separate block for each valve site. The common conduit to the reaction site is alternately a channel in a block and tubing connecting two adjacent blocks. This arrangement requires a plurality of fittings which are subject to leaking.

U.S. Pat. No. 4,773,446 discloses a valve block assembly which utilizes diaphragm valves. The valves serve to control fluid flow from a plurality of pressurized fluid reservoirs, in sequence to a common outlet reservoir. This system requires the use of conduits from the fluid reservoirs and fittings to valve blocks for each conduit. These fittings are subject to leakage.

The fluid delivery system of the prior art depend upon the use of positive pressure to deliver the fluid and upon the control of back pressure to the fluid reservoir in order to precisely control the amount of fluid delivered to a treatment reservoir. These systems require the frequent adjustment of the fluid delivery means as a function of back pressure. All of the systems set forth above depend upon the precise control of reservoir pressure and restriction through the valves to control reagent delivery volume. They are very sensitive to variations of the removable reaction columns as regards the delivery volume and flow rate. Also, these systems deliver fluids against backpressures only up to about 10 psig. It would be desirable to provide a system which eliminates the need of adjustment of the fluid delivery means. It would also be desirable to utilize a means to deliver fluids which is independent of back pressure. Such a system would permit delivery of accurate volumes of reagents which would result in improved system performance and reduced reagent consumption. It would also be desirable to provide a fluid delivery system which minimizes the use of tubes and tube fittings while minimizing the volume of the system as compared to presently available systems.

SUMMARY OF THE INVENTION

The present invention provides a plate structure fluid delivery system for delivering a plurality of fluids in sequence to a treatment reservoir wherein a chemical reaction or a physical treatment step occurs. The plate structure comprises four or five layers. A first layer includes a plurality of notched openings for receiving a fluid reservoir or a fluid treatment means, a second layer for locking the reservoir or treatment means in place and aligning the attached fluid fittings, a third layer for fluid conduits and orifices and a fourth fluid sealing layer. In one embodiment, the third layer contains only orifices and the fourth layer contains the conduits and seals the conduits from each other. In another embodiment, the third layer contains only orifices, the fourth layer contains the conduits extending through the thickness of the fourth layer and a fifth layer seals the conduits from each other. The fluids are delivered to a desired point by means of a system comprising a diaphragm pump, a diaphragm check valve and an injector, each attached to the plate structure and in direct fluid communication with the channels in the solid plate. A common outlet channel is connected to sources of a plurality of fluids and a switching means attached to the plate which directs fluid to a desired destination such as a reaction column. The switching means has the capacity to direct one or more sets of fluids to one or more desired destinations. Used fluid then is removed from the desired destination to waste.

DESCRIPTION OF SPECIFIC EMBODIMENTS

Figure 1:
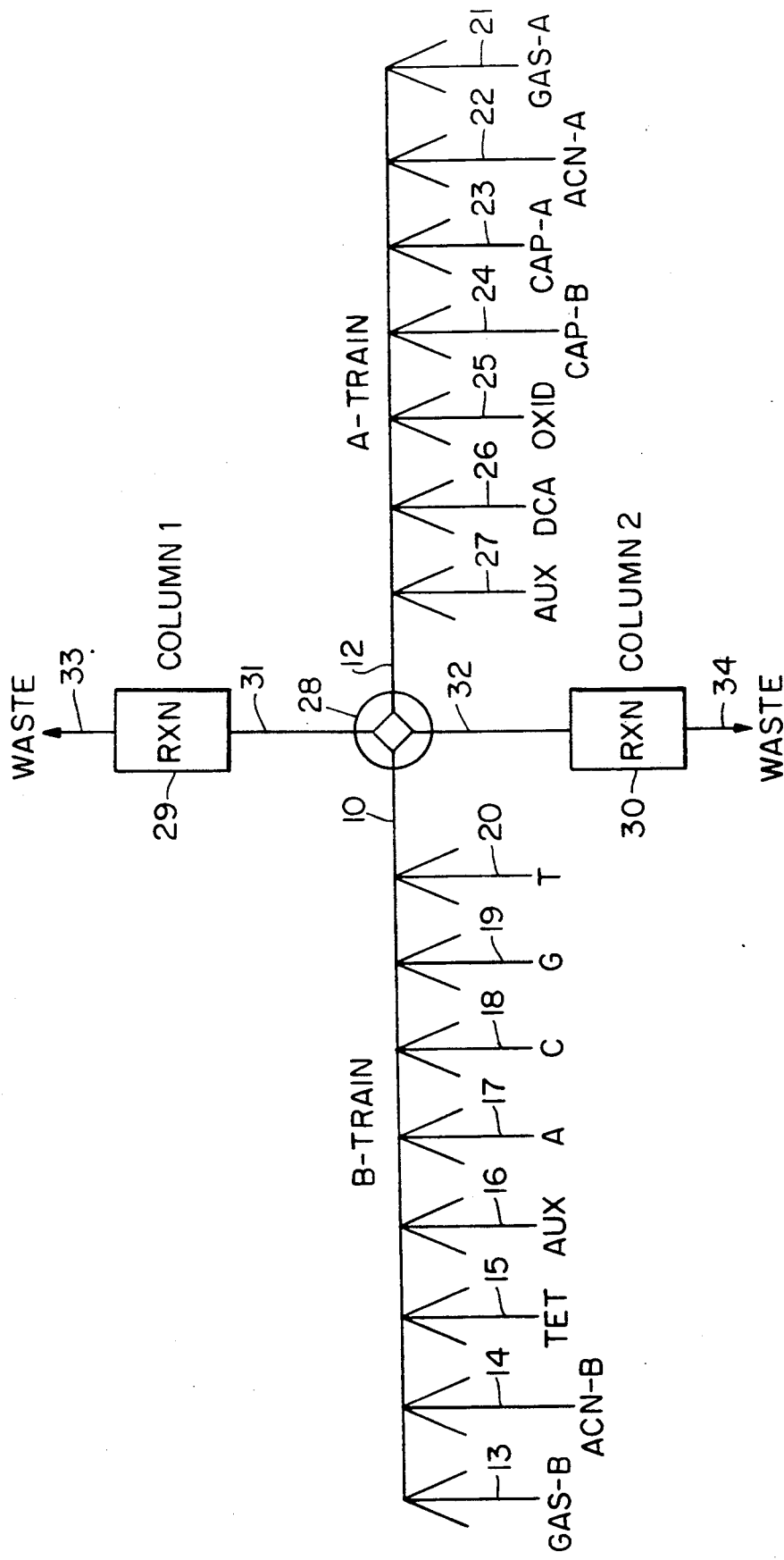
FIG. 1 is a schematic view of a system incorporating the plate structure of this invention useful for producing DNA.

In accordance with this invention, a fluid delivery system is provided which comprises a plate having conduits and fluid transport means for effecting fluid passage through the channel. The system is constructed to effect passage of a plurality of fluids in sequence through the system to at least one treatment reservoir and to maintain the fluids within the system at a desired pressure. The means for transporting each fluid comprises a check valve, a positive displacement diaphragm pump and an injector. The check valve is connected to a source of fluid and is in direct fluid communication with the diaphragm pump and the injector. The diaphragm pump functions to transport fluid from the check valve to and through the injector. Each injector in the system is in fluid communication with a common passageway which connects with a treatment reservoir where chemical reaction or physical fluid manipulation is effected. The system of this invention is particularly suitable for use in processes where sequential chemical reactions are conducted under carefully controlled conditions. Examples of such processes include nucleic acid or protein synthesis. These processes require sequential chemical reactions which are alternated with washing steps to remove excess unreacted reagent. In some instances, the reagents require a particular atmospheric environment such as an inert environment or an oxidizing environment. In these instances, gases are provided to the fluid reservoir. Therefore, these processes require fluid delivery systems wherein reagent, processing chemicals and gases are processed in a precise manner so that precise volumes of fluid are delivered to the appropriate destination within the system at the proper time and within the proper sequence. When a plurality of treatment reservoirs are utilized, switching means are provided to direct the appropriate reagent, process chemical or gas to the appropriate treatment reservoir.

The check valve, diaphragm pump and injector are utilized in conjunction with each other to deliver a precise volume of fluid from a fluid reservoir to a treatment reservoir. Suitable control means are provided to control the sequence of fluids delivered to the treatment reservoir or reservoirs.

The plate of this invention containing the channels for fluid flow is conveniently formed of a ceramic material which can be photoetched to form the channel system in the desired configuration. The plate is formed from a plurality of layers, individually formed and which are then bonded together. A first surface of the plate contains the channels while a second surface of the plate includes the fluid inlets and outlets through which fluid flow is controlled as well as the means for securing the working components of the system. The first surface of the plate is sealed to a bottom plate member such as glass or plastic. Sealing is effected to seal the channels into the desired flow configuration. The transparent plate member provides the advantage of a direct view to the channel system so that damage to the system can be observed readily.

The check valve, diaphragm pump and injector system for each fluid as well as the remaining components of the system such as the treatment reservoirs are secured by means of the first two layers of the plate in a manner so that they communicate with the appropriate fluid inlets and fluid outlets in the third layer.

The check valve comprises a housing secured to the plate which houses the working portion of the valve. The valve housing includes flanges and slots which mate with openings in the plate in order to secure the housing to the plate in a manner which permits the check valve to function.

The diaphragm pump is a positive displacement pump within a diaphragm pump housing. The diaphragm pump housing also includes flanges and slots which mate with holes in the plate to secure the diaphragm pump housing to the plate.

Figure 3:
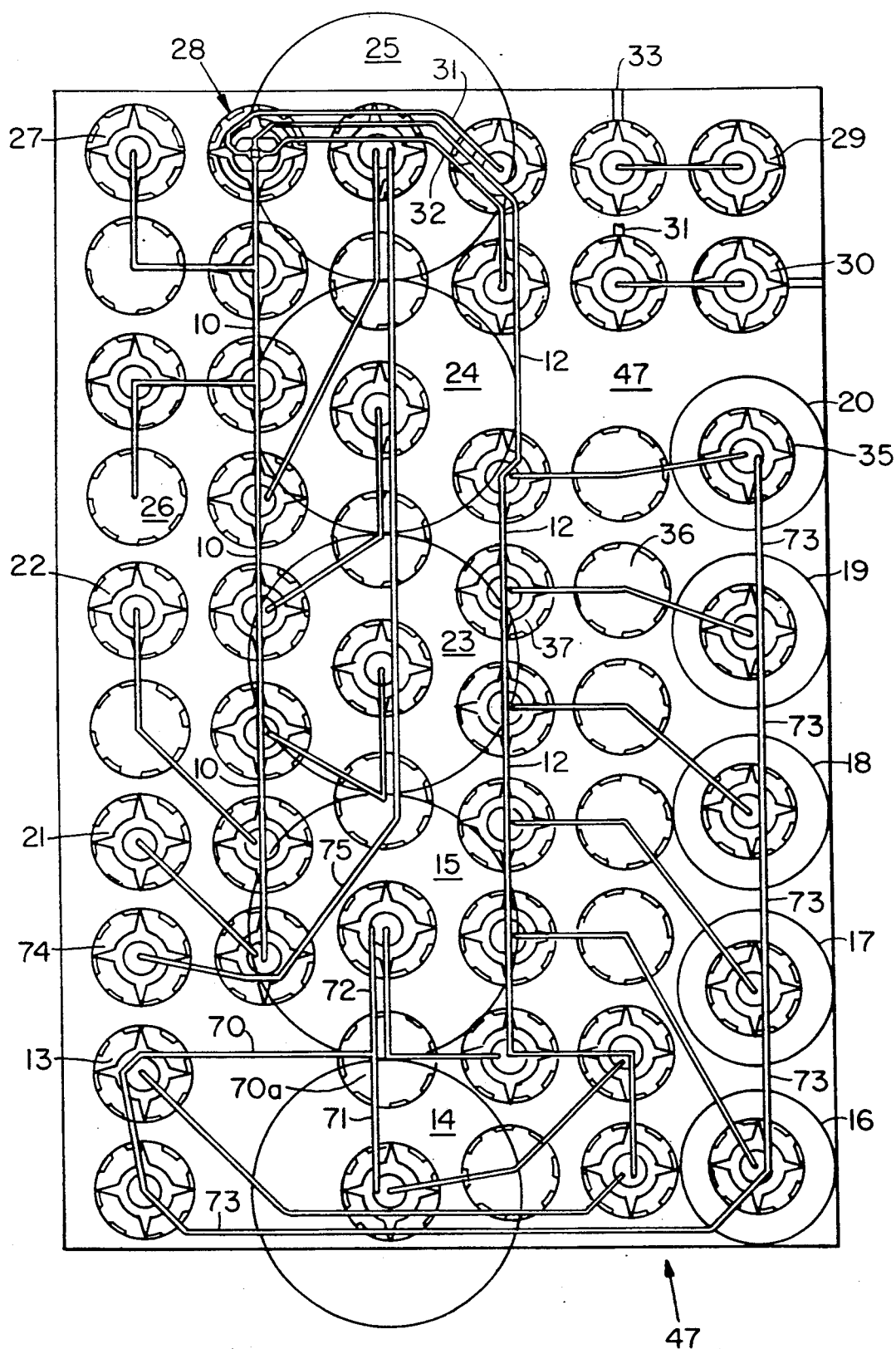
FIG. 3 is a top view of the plate structure of this invention useful for implementing the system of FIG. 1.

The injector includes an injector housing secured to the plate by means of flanges and slots in the housing which mate with holes in the plate. The housings are attached by pushing and turning them a fraction of a turn to engage the flanges on the housings with the flanges on the first layer of the plate. The system of the invention will be described with reference to a process for producing polymeric nucleic acids (NA). Referring to FIG. 1 a process for making NA is shown schematically. The process shown utilizes two sets of fluid reagents with one set in fluid communication with common channel 10 and a second set in fluid communication with common channel 12. The first set includes a gas flow-through means for purging the system, (Gas B) connected to channel 13, acetonitrile connected to channel 14, tetrazole (TET) connected to channel 15, an auxiliary reservoir (AUX) connected to channel 16, adenosine connected to channel 17, cytidine connected to channel 18, guanosine connected to channel 19 and thymidine connected to channel 20. The second set of fluids includes a gas flow-through means for purging the system (GAS-A) connected to channel 21, acetonitrile connected to channel 22, capping solution A (CAP-A) connected to channel 23, capping solution B (CAP-B) connected to channel 24, oxidizer (OXID) connected to channel 25, dichloroacetic acid (DCA) connected to channel 26 and auxiliary reagent reservoir (AUX) connected to channel 27. The reagents, adenosine, cytidine, guanosine and thymidine are reagents used to form the DNA as is well known in the art. GAS-A provides the function of purging the system and transporting small volumes of liquid out of the system to a detector. GAS-B provides the same function as GAS-A. Acetonitrile provides the function of rinsing the system. Acetic anhydride (CAP-A) and N-methylimidazole (CAP-B) provides the function of terminating unreacted sites to prevent further elongation of the failed sequence. OXID such as iodine in water and pyridine provides the function of oxidizing the elongated polymeric chain to stabilize the internucleotide phosphate linkages. DCA provides the function of deprotecting the bound residue to permit further condensation reaction. TET provides the function of activating the reactive monomer for the next coupling reaction. Referring to FIG. 3, partition valve 28 serves as a switch to direct fluid from either channel 10 or channel 12 to either treatment reservoir 29 comprising a reaction column containing a solid support such as controlled pore glass (CPG) or a membrane through channel 31 or treatment column 30 which is a duplicate of column 29 through channel 32. Channels 33 and 34 direct processed fluid to waste or a detector.

Figure 2:
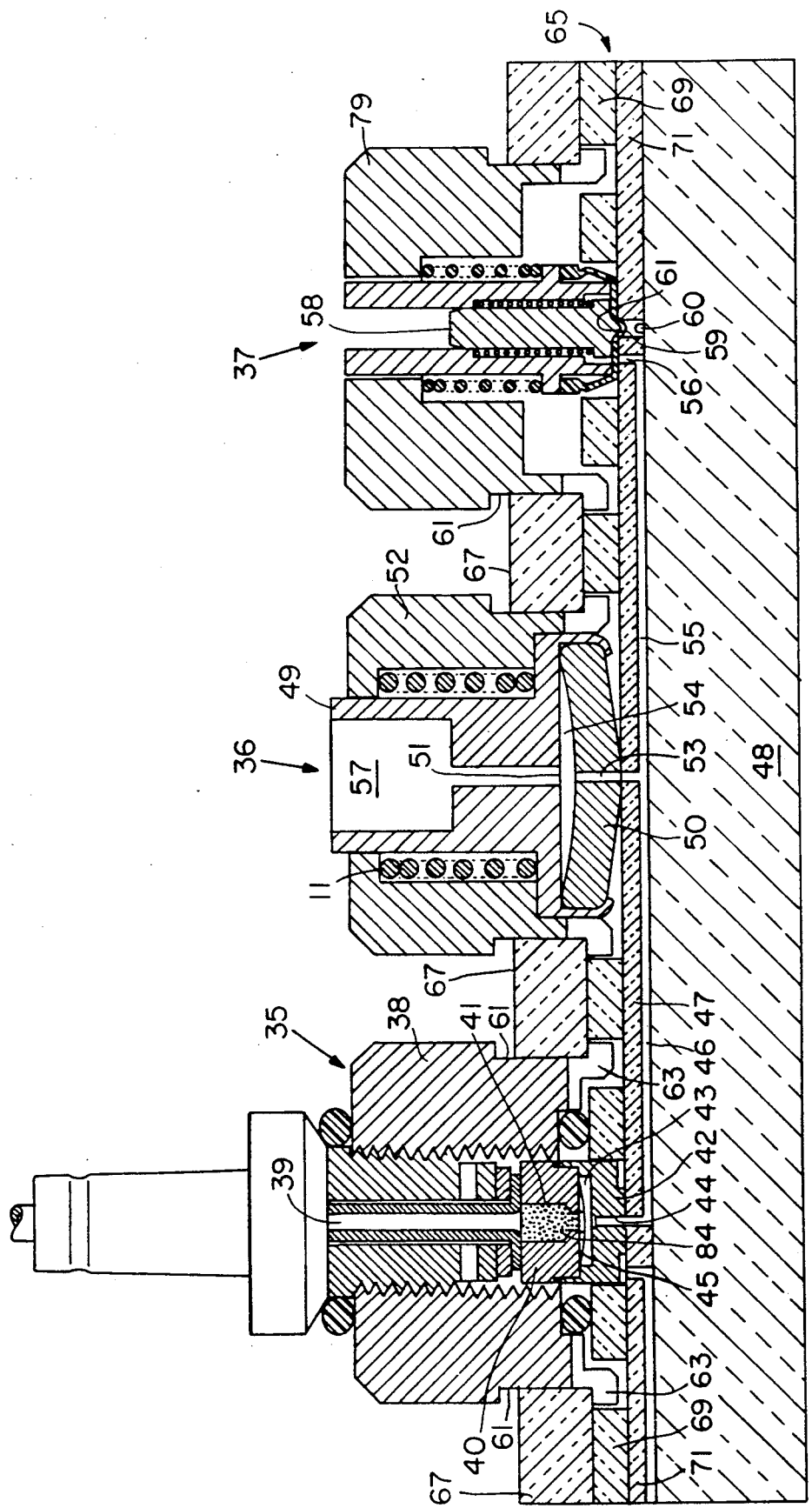
FIG. 2 is a cross-sectional view of a check valve-pump-injector unit utilized with the plate structure of this invention.

Referring to FIG. 2, the fluid delivery system of this invention is shown. The fluid delivery system comprises a check valve 35, a diaphragm pump 36 and an injector 37. The check valve 35 includes housing 38 having slots 61 and flanges 63 which mate with holes in the plate 65 formed of layers 67, 69, 71 and 48. The valve 35 has conduit 39 to accommodate a container for a fluid. A top insert 40 includes a cavity 41 housing a filtration means. A bottom insert 42 includes a plenum 43 and a check valve outlet 44. A diaphragm 45 is secured between top insert 40 and bottom insert 42. Check valve outlet 44 communicates with channel 46 formed within top plate 71. Channel 46 is sealed by bottom plate 48 which is preferably transparent. In an alternative embodiment, conduits, e.g., 46, are formed in the cover 48, not in layer 71. In another embodiment, the conduits, e.g., 46, are formed in layer 48 which is thinner than that shown in FIG. 2 and the conduits extend through the thickness of layer 48 and a fifth layer is adhered to layer 48 to seal the conduits from each other. Diaphragm pump 36 comprises a top insert member 49 and a bottom insert member 50 between which is secured diaphragm 51. The inserts 49 and 50 are positioned within housing 52. Channel 46 communicates with pump inlet 53 which, in turn, communicates with pump plenum 57. Insert 49 contains a cavity 54 to allow an attachment to a fluid reservoir which can be opened or closed to alternatively apply or reduce pressure on the top surface of the diaphragm. Pump inlet 53 communicates with channel 55 which communicates with injector inlet 56. Injector 37 includes a plunger 58, an injector diaphragm 59 and injector outlet 60. The end 61 of the plunger 58 is shaped so that the diaphragm 59 seats against outlet 60 and is positioned away from inlet 56. In use, pressure is applied to the fluid within cavity 39 (for example about 5 to 10 psig) while pressure is reduced within cavity 57. Diaphragm 45 is expanded under pressure, away from inlet 41 and fluid is expelled into outlet 44, channel 46, pump inlet 53 to fill plenum 54 which has a known, fixed volume. Applying high pressure to fluid port 57 expels fluid from plenum 54 which causes diaphragm 45 in check valve 35 to close and to cause plunger 58 to be raised and diaphragm 61 to open in injector 37. The pressureized fluid is directed into injector outlet 60. After the volume of fluid in cavity 54 has been expelled through injector outlet 60, pressure at injector inlet 56 diminishes and plunger 58 returns to the position shown in FIG. 2 wherein access from injector inlet 56 to injector outlet 60 is closed.

A function of the system of this invention is described with reference to FIG. 3 and a process for producing DNA. The elements of the plate are shown in continuous lines for convenience. The reactant adenosine, cytidine, guanosine and thymidine are housed in containers 17, 18, 19 and 20 respectively. The system of check valve 35, diaphragm pump 36 and injector 37 functions to direct adenine to channel 12 in plate 47. Duplicate systems of a check valve, a diaphragm pump and injector are utilized for the remaining reactants and are not described herein as to reduce duplication. All of these reactants however, pass from their respective storage containers into channel 12. From channel 12, the reagents pass sequentially to partition switch 28 where they are directed through conduit 31 to column attachment 29 or through conduit 32 to column attachment 30. Subsequent to reaction, the excess reagent pass to waste either through channel 33 or channel 31. Pressurized blanket gas is directed from a container (not shown) attached to and in fluid communication with fitting 13 and is directed through channel 70, 71, and 72 to containers 14 and 15 as well as through channel 73 to containers 16, 17, 18, 19 and 20. Sufficient pressure from the blanket gas is applied to open the check valves when the associated diaphragm pumps are not actuated. Similarly, blanket gas is supplied from a container (not shown) through fitting 74 through channel 75 to containers 23, 24 and 25. DCA and ACN-A reservoirs are pressurized by a separate system (not shown). Fitting 21 for Blow-A and fitting 13 for Blow-B provide a means to inject high pressure gas into the system for purging the two reagent trains.

Figure 4:
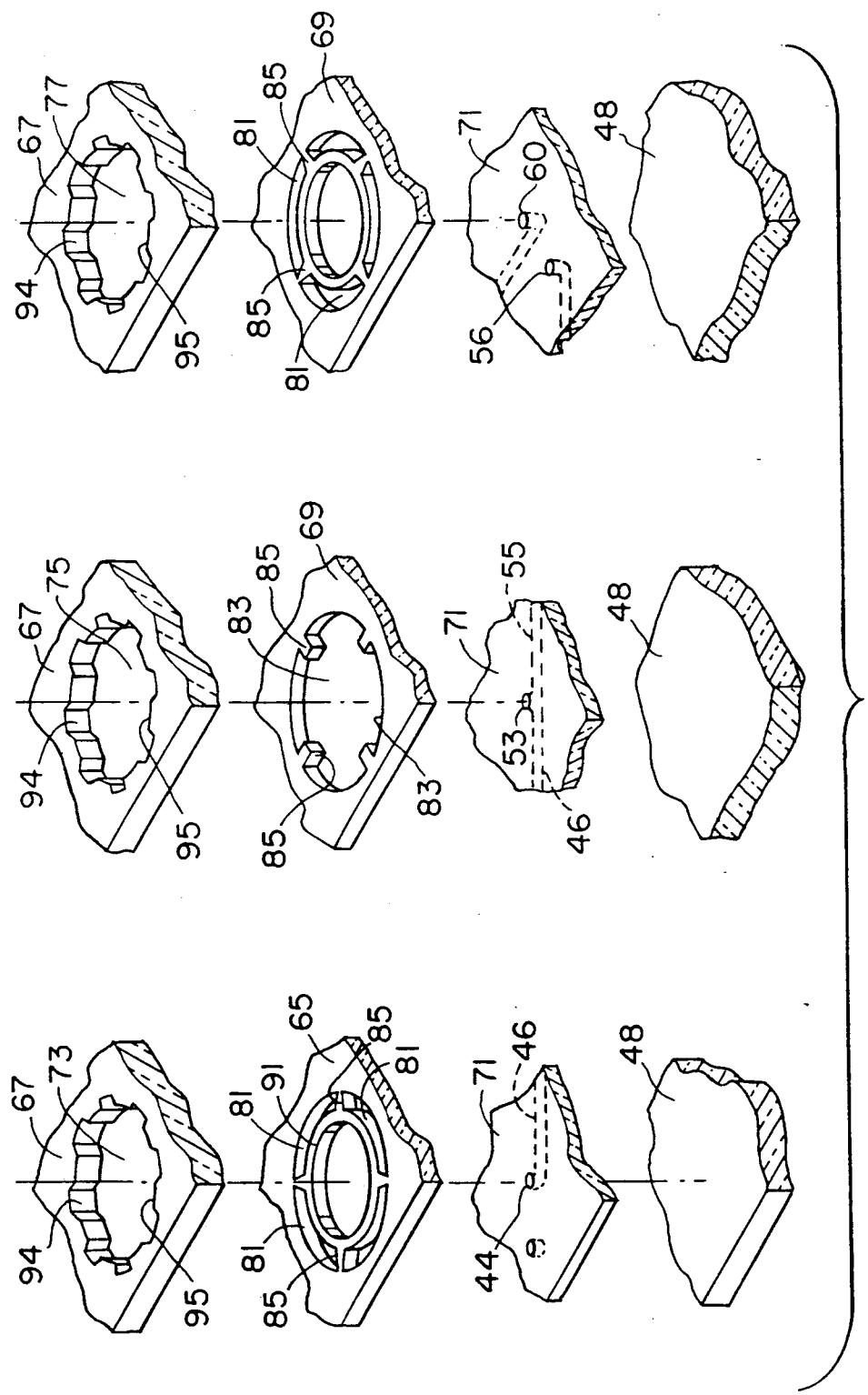
FIG. 4 is an exploded view of a plate structure for accommodating a check valve, pump or injector taken along line 4—4 of FIG. 3.

Referring to FIG. 4, the various layers of the plate of this invention are shown. The layer 67 includes holes 73, 75 and 77 for accommodating housings 38, 52 and 79 respectively (FIG. 2). Housings 38, 52 and 79 also include slots 61 and flanges 63. Layer 67 includes slots 94 and extension 95 which mate with slots 61 and flanges 63, The flanges 63 fit within slots 81 or 83 between extensions 85 in layer 69. The housings 38, 52 and 79, once inserted within slots 81 and 83 are turned so that the flanges 63 are positioned beneath extensions 95 by means of stops 85 and are retained within slots 81 and 83.

Figure 5:
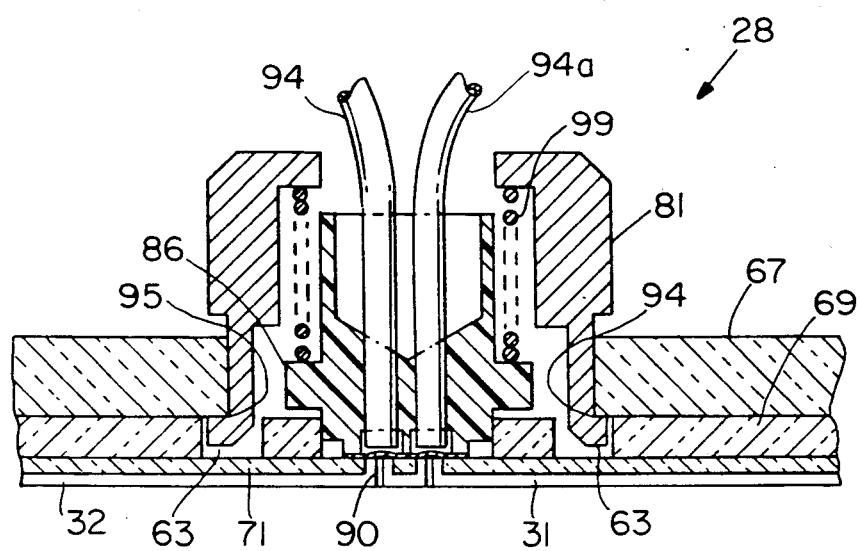
FIG. 5 is a side view, in partial cross section of a partition valve of this invention.
Figure 6:
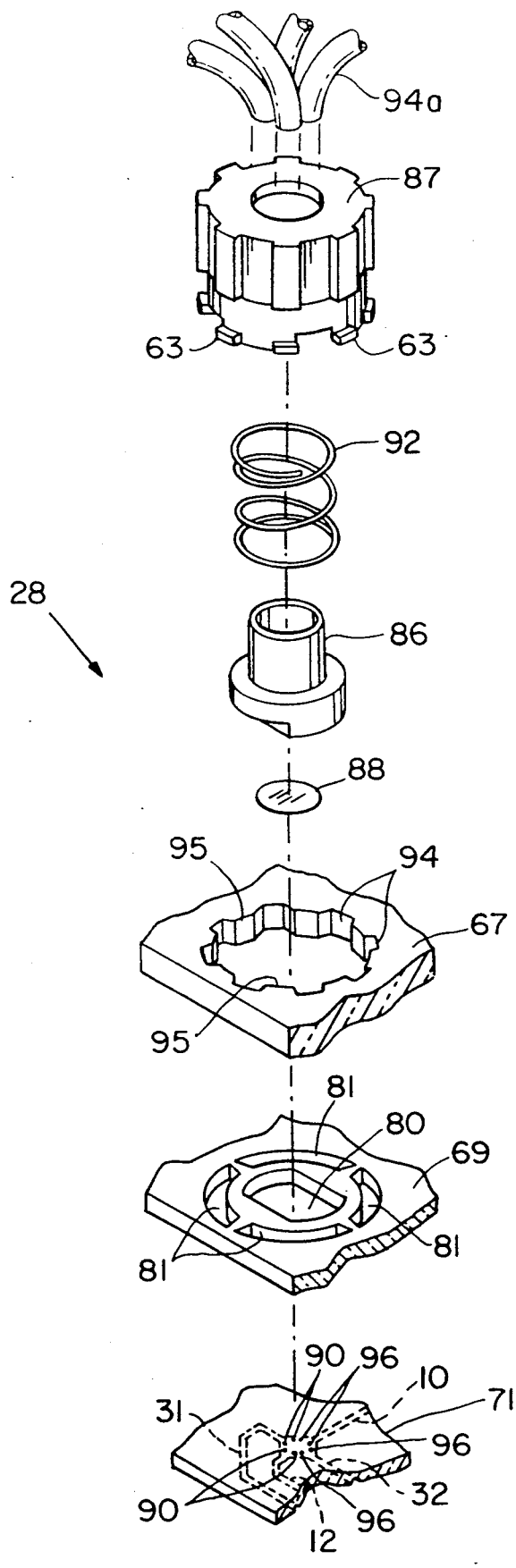
FIG. 6 is an exploded isometric view of the elements forming the partition switch of FIG. 5.

Referring to FIGS. 5 and 6, the partition valve consists of a plurality of elements. As specifically shown in FIG. 6, the ceramic plate includes layers 67, 69 and 71 as well as layer 48 (FIG. 2). Layer 71 contains channels 10, 12, 31 and 32 of partition valve 28. Layer 69 contains a central opening 80 and four peripheral openings into which flanges 63 of housing 87 fit. Layer 67 includes slots 81 into which flanges 63 fit. The housing 87 is passed through the slots 94 and then rotated so that flanges 63 are positioned under extensions 95 to retain housing 87 in place. Prior to positioning the housing 87 in place, the valve body 86 and diaphragm 88 are placed into opening 80 of layer 69 and to position partition valve diaphragm 88 over the openings 90 of layer 71. A spring 92 is provided to retain the valve body 86 in place within housing 87 and conteract the forces developed during valve operations. Four tubes 94a are positioned within valve body 86 over eight openings 90 and 96 in layer 71 which allows communication between any two of channels 10, 12, 31 and 32. By this arrangement it is possible to control communication between openings 90 selectively to effect fluid communication between channels 10 or 12 with channels 31 or 32 by exerting or removing pneumatic pressure through elected tubes 94 on selected areas of diaphragm 88.

I claim:

1. In a system for directing a plurality of fluids in sequence to a treatment reservoir a plate means which comprises:

a first layer having first holes with a periphery comprising a plurality of first flanges alternating with a plurality of first slots to accommodate a housing having second flanges and second slots, a second layer contacting said first layer having second holes axially positioned relative to said first holes to communicate with said first holes, stop means within said second layer which permit positioning said second flanges against said first flanges thereby to retain said second flanges within said second layer, a plurality of third flanges adjacent the periphery of said second holes, axially positioned so as to position a plurality of said second flanges inserted through said first holes in contact with said first flanges and said third flanges, a third layer contacting said second layer, a plurality of first passageways extending through said third layer, each of said first passageways being in fluid communication with a channel adjacent said third layer, and means adjacent said third layer for sealing said passageways to permit fluid flow through said first passageways and said channels.

2. The plate means of claims 1 wherein said means for sealing comprises a transparent plate.

3. The plate means of claims 1 wherein a raised surface is positioned on said third layer within a plurality of said second holes.

4. The plate means of claim 2 wherein a raised surface is positioned on said third layer within a plurality of said second holes.

5. The plate means of claim 1 having a plurality of common passageways, each of said common passageways in fluid communication with a plurality of said first passageways.

6. The plate means of claim 2 having a plurality of common passageways, each of said common passageways in fluid communication with a plurality of said first passageways.

7. The plate means of claim 3 having a plurality of common passageways, each of said common passageways in fluid communication with a plurality of said first passageways.

8. The plate means of claim 4 having a plurality of common passageways, each of said common passageways in fluid communication with a plurality of said first passageways.

9. The plate means of claim 5 including one first hole having a plurality of first passageways positioned to direct fluid to a plurality of said common passageways.

10. The plate means of claim 6 including one first hole having a plurality of first passageways positioned to direct fluid to a plurality of said common passageways.

11. The plate means of claim 7 including one first hole having a plurality of first passageways positioned to direct fluid to a plurality of said common passageways.

12. The plate means of claim 8 including one first hole having a plurality of first passageways positioned to direct fluid to a plurality of said common passageways.

13. The plate means of any one of claims 1, 2, 3 or 4 wherein each channel is positioned within said third layer.

14. The plate means of any one of claims 5, 6, 7, 8, 9, 10, 11 or 12 wherein each channel is positioned within said third layer.

15. The plate means of any one of claims 1, 2, 3 or 4 wherein each channel is positioned within a fourth layer in contact with said third layer.

16. The plate means of any one of claims 5, 6, 7, 8, 9, 10, 11 or 12 wherein each channel is positioned within a fourth layer in contact with said third layer.

* * * * *